(12) United States Patent
Adams et al.

(10) Patent No.: US 11,771,449 B2
(45) Date of Patent: *Oct. 3, 2023

(54) SHOCKWAVE BALLOON CATHETER SYSTEM

(71) Applicant: Shockwave Medical, Inc., Santa Clara, CA (US)

(72) Inventors: John M. Adams, Snohomish, WA (US); Daniel Hawkins, Santa Clara, CA (US); Clifton A. Alferness, Olalla, WA (US)

(73) Assignee: SHOCKWAVE MEDICAL, INC., Santa Clara, CA (US)

(*) Notice: Subject to any disclaimer, the term of this patent is extended or adjusted under 35 U.S.C. 154(b) by 393 days.

This patent is subject to a terminal disclaimer.

(21) Appl. No.: 17/190,193

(22) Filed: Mar. 2, 2021

(65) Prior Publication Data

US 2021/0282792 A1    Sep. 16, 2021

Related U.S. Application Data

(63) Continuation of application No. 16/028,225, filed on Jul. 5, 2018, now Pat. No. 10,959,743, which is a (Continued)

(51) Int. Cl.
*A61B 17/22* (2006.01)
*A61B 17/225* (2006.01)
*A61B 17/3207* (2006.01)

(52) U.S. Cl.
CPC .... *A61B 17/22022* (2013.01); *A61B 17/2202* (2013.01); *A61B 17/22029* (2013.01); (Continued)

(58) Field of Classification Search
CPC ........ A61B 17/320725; A61B 17/2202; A61B 17/22022; A61B 2017/22001; (Continued)

(56) References Cited

U.S. PATENT DOCUMENTS 3,413,976 A    12/1968 Roze
3,785,382 A    1/1974 Schmidt-Kloiber et al.
(Continued)

FOREIGN PATENT DOCUMENTS

AU    2009313507 B2    11/2014
CA    2104414 A1    2/1995
(Continued)

OTHER PUBLICATIONS

21 C.F.R. 870.5100 Title 21, vol. 8 Apr. 1, 2018 pp. 1-2.
(Continued)

*Primary Examiner* — Kathleen S Holwerda
(74) *Attorney, Agent, or Firm* — Morrison & Foerster LLP

(57) ABSTRACT

A system for breaking obstructions in body lumens includes a catheter including an elongated carrier, a balloon about the carrier in sealed relation thereto, the balloon being arranged to receive a fluid therein that inflates the balloon, and an arc generator including at least one electrode within the balloon that forms a mechanical shock wave within the balloon. The system further includes a power source that provides electrical energy to the arc generator.

12 Claims, 8 Drawing Sheets

Related U.S. Application Data continuation of application No. 14/660,539, filed on Mar. 17, 2015, now Pat. No. 10,039,561, which is a continuation of application No. 13/646,570, filed on Oct. 5, 2012, now Pat. No. 9,011,462, which is a continuation of application No. 12/482,995, filed on Jun. 11, 2009, now Pat. No. 8,956,371.

(60) Provisional application No. 61/061,170, filed on Jun. 13, 2008.

(52) U.S. Cl.
CPC ... *A61B 17/2251* (2013.01); *A61B 17/320725* (2013.01); *A61B 2017/22001* (2013.01); *A61B 2017/22021* (2013.01); *A61B 2017/22024* (2013.01); *A61B 2017/22025* (2013.01); *A61B 2017/22038* (2013.01); *A61B 2017/22058* (2013.01); *A61B 2017/22061* (2013.01); *A61B 2017/22062* (2013.01)

(58) Field of Classification Search
CPC .......... A61B 2017/22021; A61B 2017/22025; A61B 2017/22038; A61B 2017/22061; A61B 2017/22062
See application file for complete search history.

(56) References Cited

U.S. PATENT DOCUMENTS

| | | |
|---|---|---|
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,809,682 A | 3/1989 | Forssmann et al. |
| 4,813,934 A | 3/1989 | Engelson et al. |
| 4,878,495 A | 11/1989 | Grayzei |
| 4,900,303 A | 2/1990 | Lemeison |
| 4,990,134 A | 2/1991 | Auth |
| 4,994,032 A | 2/1991 | Sugiyama et al. |
| 5,009,232 A * | 4/1991 | Hassler .............. A61B 17/2256 601/4 |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,103,804 A | 4/1992 | Abele et al. |
| 5,116,227 A | 5/1992 | Levy |
| 5,152,767 A * | 10/1992 | Sypal ............... A61B 17/22022 606/128 |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyie |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,931,805 A | 8/1999 | Brisken |
| 6,007,530 A | 12/1999 | Domhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,113,560 A | 9/2000 | Simnacher |
| 6,132,444 A | 10/2000 | Shturman et al. |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 † | 4/2002 | Healy |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Comish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,309,324 B2 † | 12/2007 | Hayes |
| 7,505,812 B1 | 3/2009 | Eggers et al. |
| 7,569,032 B2 † | 8/2009 | Naimark |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 * | 2/2015 | Hawkins ............. A61B 17/2202 601/4 |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,333,000 B2 | 5/2016 | Hakala et al. |
| 9,421,025 B2 | 8/2016 | Hawkins et al. |
| 10,039,561 B2 | 8/2018 | Adams et al. |
| 10,149,690 B2 | 12/2018 | Hawkins et al. |
| 10,702,293 B2 * | 7/2020 | Adams ............... A61B 17/2202 |
| 10,959,743 B2 | 3/2021 | Adams et al. |
| 11,000,299 B2 | 5/2021 | Hawkins et al. |
| 11,534,187 B2 | 12/2022 | Bonutti |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |

(56) References Cited

U.S. PATENT DOCUMENTS

| | | | |
|---|---|---|---|
| 2003/0176873 A1 | 9/2003 | Chernenko et al. |
| 2003/0229370 A1 | 12/2003 | Miller |
| 2004/0044308 A1 | 3/2004 | Nairnark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0074484 A1 | 4/2006 | Huber |
| 2006/0184076 A1 | 8/2006 | Gill et al. |
| 2006/0190022 A1† | 8/2006 | Beyar |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0239082 A1† | 10/2007 | Schultheiss |
| 2007/0239253 A1 | 10/2007 | Jagger et al. |
| 2007/0244423 A1 | 10/2007 | Zumeris et al. |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0247945 A1 | 10/2009 | levit et al. |
| 2009/0254114 A1 | 10/2009 | Hirszowicz et al. |
| 2010/0016862 A1 | 1/2010 | Hawkins et al. |
| 2010/0036294 A1† | 2/2010 | Mantell |
| 2010/0094209 A1 | 4/2010 | Drasler et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2012/0071889 A1 | 3/2012 | Mantell et al. |
| 2012/0095461 A1 | 4/2012 | Herscher et al. |
| 2012/0143177 A1 | 6/2012 | Avitall et al. |
| 2012/0203255 A1 | 8/2012 | Hawkins et al. |
| 2012/0253358 A1 | 10/2012 | Golan et al. |
| 2013/0030431 A1 | 1/2013 | Adams |
| 2014/0005576 A1 | 1/2014 | Adams et al. |
| 2014/0039513 A1 | 2/2014 | Hakala et al. |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0073430 A1 | 3/2015 | Hakala et al. |
| 2015/0320432 A1 | 11/2015 | Adams |
| 2016/0151081 A1 | 6/2016 | Adams et al. |
| 2016/0183957 A1 | 6/2016 | Hakala et al. |
| 2021/0338258 A1 | 11/2021 | Hawkins et al. |

FOREIGN PATENT DOCUMENTS

| | | |
|---|---|---|
| CN | 1269708 A | 10/2000 |
| CN | 101043914 A | 9/2007 |
| CN | 102057422 A | 5/2011 |
| CN | 102271748 A | 12/2011 |
| CN | 102765785 A | 11/2012 |
| DE | 3038445 A1 † | 5/1982 |
| DE | 3038445 A1 | 5/1982 |
| EP | 442199 A2 | 8/1991 |
| EP | 0571306 A † | 11/1993 |
| EP | 571306 A1 | 11/1993 |
| EP | 623360 A1 | 11/1994 |
| EP | 2253884 A1 | 11/2010 |
| EP | 2362798 B1 | 4/2014 |
| JP | 62-99210 U | 6/1987 |
| JP | S62-275446 † | 11/1987 |
| JP | S62-275446 A | 11/1987 |
| JP | 3-63059 A | 3/1991 |
| JP | 6-125915 A | 5/1994 |
| JP | H7-47135 A | 2/1995 |
| JP | H8-89511 A | 4/1996 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-081374 A | 3/2004 |
| JP | 2004-357792 A | 12/2004 |
| JP | 2008-506447 A | 12/2004 |
| JP | 2011-513694 A | 12/2004 |
| JP | 2011-520248 A | 12/2004 |
| JP | 2005-095410 A | 4/2005 |
| JP | 2005-515825 A | 6/2005 |
| JP | 2006-516465 A | 7/2006 |
| JP | 2007-532182 A | 11/2007 |
| JP | 2011-524203 A | 9/2011 |
| JP | 2011-528963 A | 12/2011 |
| JP | 2012-505050 A | 3/2012 |
| JP | 2012-508042 A | 4/2012 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999002096 A1 | 1/1999 |
| WO | WO-2004069072 A2 | 8/2004 |
| WO | WO-2005099594 A1 | 10/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009152352 A2 | 12/2009 |
| WO | WO-2010014515 A2 | 2/2010 |
| WO | WO-2010054048 A2 | 5/2010 |
| WO | WO-2010014515 A3 | 8/2010 |
| WO | WO-2010054048 A3 | 9/2010 |
| WO | WO-2011143468 A2 | 11/2011 |
| WO | WO-2012025833 A2 | 3/2012 |
| WO | WO-2014025620 A1 | 2/2014 |

OTHER PUBLICATIONS

Advisory Action received for U.S. Appl. No. 13/615,107, dated Nov. 6, 2015, 3 pages.
Advisory Action Received for U.S. Appl. No. 12/482,995, dated Jun. 2, 2014, 3 pages.
Advisory Action Received for U.S. Appl. No. 12/482,995, dated Sep. 29, 2011, 2 pages.
Advisory Action Received for U.S. Appl. No. 12/581,295, dated Jul. 3, 2014, 3 pages.
Advisory Action Received for U.S. Appl. No. 13/049,199, dated Jun. 7, 2012, 3 pages.
Advisory Action received for U.S. Appl. No. 13/267,383, dated Jan. 6, 2014, 4 pages.
After Orbital Atherectomy Video (post treatment) Video 2019.
Amendment After Final Action received for U.S. Appl. No. 12/482,995, filed May 16, 2014, 8 pages.
Amendment in Response to Non-Final Office Action received for U.S. Appl. No. 12/482,995, filed Jan. 9, 2014 Jan. 9, 2014, 9 pages.
Amighi et al., (2005). "Impact of the Rapid-Exchange Versus Over-the-Wire Technique on Procedural Complications of Renal Artery Angioplasty," J Endovasc Ther., 12:233-239.

(56) References Cited

OTHER PUBLICATIONS

Armstrong, Ehrin Responses to Question 6 by Patent Owner's Declarants Ehrin Armstrong, Jan. 29, 2020, 5 pages.
Armstrong, Ehrin Responses to Questions 1-5 by Patent Owner's Declarants Ehrin Armstrong, Jan. 24, 2020, 4 pages.
Athanasoulis, (1980). "Percutaneous Transluminal Angioplasty: General Principles," American journal of Roentgenology, 135:893-900.
Bank of America Merrill Lynch a Simple Solution to a Difficult (and Large) Problem—Initiating Coverage of SWAV Shockwave Medical Inc., Apr. 1, 2019, pp. 1-22.
Becker et al., (1988). "Radiofrequency Balloon Angioplasty," Rationale and Proof of Principle Investigative Radiology, 23(11):810-817.
Before Orbital Aterectomy Video (pre-treatment) Video 2019.
Ben-Dor et al., "Handbook of Shock Waves", Shockwave Medical, Inc. Patent Owner Exhibit 2223, vol. 2, 2001, 824 pages.
Bittl et al., (1993). "Coronary Artery Perforation during Excimer Laser Coronary Angioplasty," Journal of the American College of Cardiology, 21(5):1158-1165.
Bittl et al., (1993). "Publication Information—Coronary Artery Perforation during Excimer Laser Coronary Angioplasty," Journal of the American College of Cardiology, 21(5): 1-6.
Brinton et al., (2016). "Publication Information—TCT-777 Safety and Performance of the Shockwave Medical Lithoplasty® System in Treating Calcified Peripheral Vascular Lesions: 6-Month Results from the Two-Phase DISRUPT PAD Study," Journal of the American College of Cardiology, 68(18):1-5.
Brinton et al., (2016). "TCT-777 Safety and Performance of the Shockwave Medical Lithoplasty® System in Treating Calcified Peripheral Vascular Lesions: 6-Month Results from the Two-Phase DISRUPT PAD Study," Journal of the American College of Cardiology, 68(18):B314.
Brodmann et al., (2018). "Primary outcomes and mechanism of action of intravascular lithotripsy in calcified femoropopliteal lesions: Results of the Disrupt PAD II Catheter ," Cardiovasc Interv., 93(2):335-342.
Calcium in the Peripheral and Coronary Arteries: The Pathologist View, Deposition Exhibit from Deposition of Dr. Finn, Mar. 6, 2020, 27 pages.
Canfield et al., (2018). "40 Years of Percutaneous Coronary Intervention: History and Future Directions," Journal of Personalized Medicine, 8(33):1-9.
Cardiology Today's Intervention Shockwave Attracts Additional Investment from Abiomed, has IPO Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo> Mar. 12, 2019, pp. 1-2.
Chart of Mantell Detailed Mapping of Provisional to '371 Claims Case No. IPR2019- 00405 2020, 12 pages.
Das et al., (2014). "Technique Optimization of Orbital Atherectomy in Calcified Peripheral Lesions of the Lower Extremities," Catheterization and Cardiov Interv, 83:115-122.
Deagon, Brian Technology—Shockwave Medical IPO Soars on First Day of Trading Investor's Business Daily, Available Online at <https://www.investors.com/news/technology/shockwave-medical-ipo-soars-trading/> Mar. 7, 2019, pp. 1-15.
Decision Instituting Inter Partes Review for U.S. Pat. No. 8,956,371, by the Patent Trial and Appeal Board dated Jul. 9, 2019, 28 pages.
Decision of Appeals Notice received for Japanese Patent Application No. 2011-534914, dated Oct. 17, 2016, 2 pages of Official Copy only.
Decision to Grant received for European Patent Application No. 13756766.5, dated May 27, 2016, 2 pages.
Decision to Grant received for European Patent Application No. 09763640.1, dated Feb. 22, 2018, 2 pages.
Decision to Grant received for European Patent Application No. 09825393.3, dated Mar. 13, 2014, 2 pages.
Decision to Grant received for Japanese Patent Application No. 2011-513694, dated Oct. 7, 2014, 3 pages of official copy only.
Declaration and CV of Aloke V. Finn Case IPR2019-00405 Feb. 20, 2020, 45 pages.
Declaration and CV of Jeffrey Chambers Case IPR2019-00405 Dec. 19, 2020, 32 pages.
Declaration of Dr. Morten Olgaard Jensen dated Dec. 6, 2018, pp. 1-137.
Declaration of Juanita DeLoach Exhibit 1236, Case IPR2019-00408 Feb. 18, 2020, 4 pages.
Declaration of Natalie J. Grace dated Apr. 10, 2019, pp. 1-3.
Deposition Exhibit from Deposition of Dr. Jensen, Balloon Attributes that Impact Deliverability, Mar. 4, 2020, 1 page.
Deposition Exhibit from Deposition of Dr. Jensen, Diagram from Wikipedia Page for Balloon Catheters, Mar. 4, 2020, 1 page.
Deposition Exhibit from Deposition of Dr. Jensen, Figures 1 and 2 of JP Patent No. 62-275446 (color added), Mar. 4, 2020, 1 page.
Deposition Exhibit from Deposition of Dr. Jensen, Handwritten Diagram, Mar. 4, 2020, 1 page.
Deposition Exhibit of Ronald David Berger Case No. IPR2019-00405 Jan. 27, 2020, 42 pages.
Deposition Transcript (compressed) of Dr. Aloke Finn, Case No. IPR2019-00405, Mar. 6, 2020, 31 pages.
Deposition Transcript (compressed) of Dr. Daniel van der Weide, Case No. IPR2019- 00409, U.S. Pat. No. 8,728,091 B2, Jan. 10, 2020., 111 pages.
Deposition Transcript (compressed) of Dr. Jeffrey Chambers, Case No. IPR2019-00405, Mar. 2, 2020., 81 pages.
Deposition Transcript (compressed) of Dr. Morten Olgaard Jensen, Case No. IPR2019-00405, U.S. Pat. No. 8,956,371, Mar. 4, 2020, 73 pages.
Deposition Transcript (compressed) of Dr. Morten Olgaard Jensen, Case No. IPR2019-00408, U.S. Pat. No. 9,642,673, Feb. 26, 2020., 80 pages.
Deposition Transcript (compressed) of Ronald David Berger Case No. IPR2019-00405 Jan. 27, 2020, 103 pages.
Dewhirst et al., (2003). "Basic Principles of Thermal Dosimetry and Thermal Thresholds for Tissue Damage from Hyperthermia International," Journal of Hyperthermia, 19(3):267-294.
Dewhirst et al., (2003). "Publication Information—Basic Principles of Thermal Dosimetry and Thermal Thresholds for Tissue Damage from Hyperthermia," International Journal of Hyperthermia, 19(3):1-3.
Diamondback 360® Peripheral Orbital Atherectomy System, Cardiovascular Systems, Inc., Patent Owner Exhibit 2231, 2019, 58 pages.
Dictionary.com Definition of 'Angioplasty' Available Online at <https://www.dictionary.com/browse/angioplasty> pp. 1-5.
Dodd, (1842). "Two Cases of Calculus in the Bladder, in Which Lithotripsy Was Performed," Provincial Medical & Surgical Journal, 3(71):368-370.
Dodge Jr., et al., (1992). "Lumen Diameter of Normal Human Coronary Arteries," Influence of Age, Sex, Anatomic Variation, and Left Ventricular Hypertrophy or Dilation Circulation, 86(1):232-246.
E-mail from Cook Alciati to Mark Nelson confirming Dr. Chamber's total compensation amount from *Cardiovascular Systems, Inc, CSI* v. *Shockwave*—Dr. Chambers Testimony, Mar. 20, 2020, 1 page.
Extended European Search Report (includes Supplementary European Search Report and Search Opinion) received for European Patent Application No. 09763640.1, dated Oct. 10, 2013, 5 pages.
Extended European Search Report and Search Opinion received for European Patent Application No. 09825393.3, dated Feb. 28, 2013, 6 pages.
Extended European Search Report received for European Patent Application No. 13827971.6, dated Apr. 12, 2016, 8 pages.
Farb et al., (2002). "Morphological Predictors of Restenosis After Coronary Stenting in Humans," Circulation, pp. 2974-2980.
FDA Clears Lithoplasty Balloon That Shatters Calcified Lesions With Ultrasound Diagnostic and Interventional Cardiology, Available Online at <https://www.dicardiology.com/product/fda-clearslithoplasty-balloon-shatters-calcified-lesions-ultrasound> Sep. 16, 2016, pp. 1-5.

(56) References Cited

OTHER PUBLICATIONS

Fernandes et al., (2007). "Enhanced infarct border zone function and altered mechanical activation predict inducibility of monomorphic ventricular tachycardia in patients with ischemic cardiomyopathy," Radiology, 245(3):712-719.
File History of U.S. Pat. No. 8,956,371, pp. 1-1561.
Final Office Action received for U.S. Appl. No. 12/482,995, dated Jul. 22, 2011, 14 pages.
Final Office Action received for U.S. Appl. No. 12/611,997, dated Dec. 11, 2012, 9 pages.
Final Office Action received for U.S. Appl. No. 12/611,997, dated Nov. 10, 2011, 15 pages.
Final Office Action received for U.S. Appl. No. 13/049,199, dated Apr. 4, 2012, 10 pages.
Final Office Action received for U.S. Appl. No. 13/207,381, dated Nov. 2, 2012, 7 pages.
Final Office Action received for U.S. Appl. No. 14/271,342 dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 12/611,997, dated Oct. 24, 2013, 10 pages.
Final Office Action received for U.S. Appl. No. 13/049,199 dated Aug. 11, 2014, 8 pages.
Final Office Action received for U.S. Appl. No. 13/207,381, dated Nov. 7, 2013, 7 pages.
Final Office Action Received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107 dated Sep. 1, 2015, 9 pages.
Final Office Action received for U.S. Appl. No. 13/646,570, dated Dec. 23, 2014, 10 pages.
Final Office Action received for U.S. Appl. No. 14/229,735, dated Aug. 27, 2015, 7 pages.
Final Office Action received for U.S. Appl. No. 15/213,105, dated May 4, 2018, 8 pages.
Final Office Action received for U.S. Appl. No. 14/660,539, dated Aug. 3, 2017, 11 pages.
Final Written Decision *Ariosa Diagnostics Inc.* vs. *Illumina Inc.* dated Jan. 7, 2016, pp. 1-18.
Final Written Decision for U.S. Pat. No. 8,956,371, by the Patent Trial and Appeal Board dated Jul. 8, 2020, 89 pages.
Fung, Y. C. Biomechanics—Mechanical Properties of Living Tissues Second Edition, Springer 1993, 14 pages.
Gottlieb, Scott U.S. Department of Health and Human Services, Food and Drug Administration Report to Congress by Scott Gottlieb Exhibit 1217 Sep. 30, 2018, 10 pages.
Grocela et al., (1997). "Intracorporeal Lithotripsy," Instrumentation and Development Urologic Clinics of North America, 24(1):13-23.
Hawkins, et al. U.S. Appl. No. 61/061,170, filed Jun. 13, 2008, titled "Shockwave Balloon Catheter System".
Hill, Jonathan M., Deposition Transcript (compressed) of Jonathan M. Hill, M.D. Exhibit 1211, Case No. IPR2019-00408, U.S. Pat. No. 9,642,673 Dec. 16, 2019, 63 pages.
Hodges et al., (1994). "Publication Information—Ultrasound Determination of Total Arterial Wall Thickness," Journal of Vascular Surgery, 19(4):1-13.
Hodges et al., (1994). "Ultrasound Determination of Total Arterial Wall Thickness," Journal of Vascular Surgery, 19(4):745-753.
Huang et al., (1998). "Cost Effectiveness of Electrohydraulic Lithotripsy v Candela Pulsed-Dye Laser in Management of the Distal Ureteral Stone," Journal of Endourology, 12(3):237-240.
Intention to Grant received for European Patent Application No. 09763640.1, dated Oct. 11, 2017, 8 pages.

Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2009/063354, dated May 19, 2011, 6 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987 dated Nov. 20, 2014, 11 pages.
International Preliminary Report on Patentability received for PCT Patent Application No. PCT/US2013/048277 dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533 dated Mar. 26, 2015, 10 pages.
International Search Report and Written Opinion received for PCT Patent Application No. PCT/US2013/031805 dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088 dated Jul. 16, 2015, 13 pages.
International Search Report received for PCT Patent Application No. PCT/US2009/047070, dated Jan. 19, 2010, 4 pages.
International Search Report received for PCT Patent Application No. PCT/US2009/063354, dated Jun. 11, 2010, 3 pages.
International Search Report received for PCT Patent Application No. PCT/US2012/023172, dated Sep. 28, 2012, 3 pages.
International Written Opinion received for PCT Patent Application No. PCT/US2009/063354, dated Jun. 11, 2010, 4 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
International Written Opinion received for PCT Patent Application No. PCT/US2009/047070, dated Jan. 19, 2010, 5 pages.
Jahnke et al., (2008). "Retrospective Study of Rapid-Exchange Monorail Versus Over-the-Wire Technique for Femoropopliteal Angioplasty," Cardiovascular and Interventional Radiology, 31:854-859.
Johnston et al., (2004). "Publication Information—Non-Newtonian Blood Flow in Human Right Coronary Arteries: Steady State Simulations," Journal of Biomechanics, 37(5):1-2.
Johnston et al., (2006). "Non-Newtonian Blood Flow in Human Right Coronary Arteries: Transient Simulations," Journal of Biomechanics, 39(6):1-35.

(56) References Cited

OTHER PUBLICATIONS

Kaplan et al., (1993). "Healing after Arterial Dilatation with Radiofrequency Thermal and Nonthermal Balloon Angioplasty Systems," Journal of Investigative Surgery, 6:33-52.

Kereiakes, Dean J., Deposition Transcript (compressed) of Dean J. Kereiakes Exhibit 1213, Cases No. 2019-00405, 00408 and 00409 Jan. 7, 2020, 65 pages.

Knuttinen et al., (2014). "Unintended Thermal Injuries from Radiofrequency Ablation: Organ Protection with an Angioplasty Balloon Catheter in an Animal Model," Journal of Clinical Imaging Science, 4(1):1-6.

Lee et al., (1991). "Structure-Dependent Dynamic Mechanical Behavior of Fibrous Caps From Human Atherosclerotic Plaques," Circulation, 83(5):1764-1770.

Lee et al., (2017). "Orbital atherectomy for treating de novo, severely calcified coronary lesions: 3-year results of the pivotal ORBIT II trial," Cardiovascular Revascularization Medicine, 18:261-264.

Lee et al., (2018). "Acute Procedural Outcomes of Orbital Atherectomy for the Treatment of Profunda Femoris Artery Disease: Subanalysis of the CONFIRM Registries," J Invasive Cardio, 330(5):177-181.

Linnemeier et al., (1993). "Radiation Exposure: Comparison of Rapid Exchange and Conventional Over-the-Wire Coronary Angioplasty Systems," Catheterization and Cardiovascular Diagnosis, 30:11-14.

Lipowski, et al. U.S. Appl. No. 61/051,262 pp. 1-36.

Liu et al., (2015). "Current Understanding of Coronary Artery Calcification," Journal of Geriatric Cardiology, 12:668-675.

Med Device Online Angioplasty Balloons Advanced Polymers Inc., Available Online at <https://www.meddeviceonline.com/doc/angioplasty-balloons-0001>, 1 page.

MedlinePlus Angioplasty U.S. National Library of Medicine, Available Online at <https://medlineplus.gov/angioplasty.html>, pp. 1-4.

Meraj et al., (2018). "Clinical outcomes of Atherectomy Prior to Percutaneous Coronary Intervention: A Comparison of Outcomes following Rotational Versus Orbital Atherectomy (COAP-PCI study)," Journal of Interventional Cardiology, 31:478-485.

Mills et al., (2019). "Cracking the Code on Calcium; Initiate with BUY, $39 Target Canaccord Genuity—Capital Markets," US Equity Research Apr. 1, 2019, pp. 1-63.

Mitomo, "Intravascular lithotripsy: A Novel Technology for Treating Calcified Coronary Stenoses Cardiovascular News," Online Available at <https://cardiovascularnews.com/intravascular-lithotripsy-anovel-technology-for-treating- calcified-coronary-stenoses> Apr. 18, 2018, pp. 1-4.

Mooney et al., (1990). "Monorail Piccolino Catheter: A New Rapid Exchange/Ultralow Profile Coronary Angioplasty System," Catheterization and Cardiovascular Diagnosis, 20:114-119.

Mori et al., "Coronary Artery Calcification and its Progression—What Does it Really Mean", American College of Cardiology Foundation, vol. 11, No. 1, 2018, 16 pages.

Myler et al., (1987). "Recurrence After Coronary Aangioplasty," Catheterization and Cardiovascular Diagnosis, 13:77-86.

Nichols et al., (2005). "McDonald's Blood Flow in Arteries: Theoretical," Experimental and Clinical Principles 5th Edition, pp. 1-9.

Nisonson et al., (1986). "Ambulatory Extracorporeal Shockwave Lithotripsy," Urology, 28(5):381-384.

Non Final Office Action received for U.S. Appl. No. 12/482,995, dated Aug. 13, 2014, 10 pages.

Non Final Office Action received for U.S. Appl. No. 12/482,995, dated Jul. 12, 2013, 11 pages.

Non Final Office Action received for U.S. Appl. No. 12/611,997, dated Nov. 26, 2014, 8 pages.

Non Final Office Action received for U.S. Appl. No. 13/207,381, dated Nov. 25, 2014, 5 pages.

Non Final Office Action received for U.S. Appl. No. 13/465,264, dated Oct. 29, 2014, 13 pages.

Non Final Office Action received for U.S. Appl. No. 13/646,570, dated Oct. 29, 2014, 10 pages.

Non Final Office Action received for U.S. Appl. No. 14/079,463, dated Mar. 4, 2014, 9 pages.

Non Final Office Action received for U.S. Appl. No. 12/482,995, dated Feb. 11, 2011, 27 pages.

Non Final Office Action received for U.S. Appl. No. 12/611,997, dated Apr. 8, 2013, 9 pages.

Non Final Office Action received for U.S. Appl. No. 12/611,997, dated Aug. 24, 2012, 11 pages.

Non Final Office Action received for U.S. Appl. No. 12/611,997, dated Jun. 21, 2011, 13 pages.

Non Final Office Action received for U.S. Appl. No. 13/049,199, dated Dec. 12, 2011, 10 pages.

Non Final Office Action received for U.S. Appl. No. 13/207,381, dated Feb. 22, 2013, 7 pages.

Non Final Office Action received for U.S. Appl. No. 13/207,381, dated Jun. 12, 2012, 6 pages.

Non Final Office Action received for U.S. Appl. No. 13/534,658, dated Mar. 11, 2016, 12 pages.

Non Final Office Action received for U.S. Appl. No. 14/218,858, dated Mar. 30, 2016, 13 pages.

Non Final Office Action received for U.S. Appl. No. 14/515,130, dated Jan. 14, 2016, 16 pages.

Non-Final Office Action received for U.S. Appl. No. 12/501,619, dated Jan. 28, 2014, 10 pages.

Non-Final Office Action received for U.S. Appl. No. 12/581,295, dated Jan. 15, 2015, 14 pages.

Non-Final Office Action received for U.S. Appl. No. 12/581,295, dated Mar. 10, 2014, 11 pages.

Non-Final Office Action received for U.S. Appl. No. 12/611,997, dated Feb. 13, 2014, 9 pages.

Non-Final Office Action received for U.S. Appl. No. 13/049,199, dated Feb. 4, 2014, 8 pages.

Non-Final Office Action received for U.S. Appl. No. 13/207,381, dated Feb. 25, 2014, 8 pages.

Non-Final Office Action received for U.S. Appl. No. 13/267,383, dated Feb. 25, 2015, 9 pages.

Non-Final Office Action received for U.S. Appl. No. 13/465,264, dated Dec. 23, 2014, 13 pages.

Non-Final Office Action received for U.S. Appl. No. 13/615,107, dated Apr. 24, 2015, 9 pages.

Non-Final Office Action received for U.S. Appl. No. 13/646,583, dated Oct. 31, 2014, 8 pages.

Non-Final Office Action received for U.S. Appl. No. 14/061,554, dated Mar. 12, 2014, 14 pages.

Non-Final Office Action received for U.S. Appl. No. 14/271,276, dated Aug. 4, 2014, 7 pages.

Non-Final Office Action received for U.S. Appl. No. 14/271,342, dated Sep. 2, 2014, 6 pages.

Non-Final Office Action received for U.S. Appl. No. 14/273,063, dated Jun. 3, 2016, 9 pages.

Non-Final Office Action received for U.S. Appl. No. 14/660,539, dated Nov. 24, 2017, 10 pages.

Non-Final Office Action received for U.S. Appl. No. 14/693,155, dated Jan. 15, 2016, 6 pages.

Non-Final Office Action received for U.S. Appl. No. 15/213,105, dated Nov. 28, 2017, 7 pages.

Non-Final Office Action received for U.S. Appl. No. 14/660,539, dated Mar. 6, 2017, 14 pages.

Notice of Acceptance Received for Australian Patent Application No. 2009257368, dated Aug. 28, 2014, 2 pages.

Notice of Acceptance Received for Australian Patent Application No. 2009313507, dated Nov. 17, 2014, 2 pages.

Notice of Allowance received for Canadian Patent Application No. 2,727,429, dated May 26, 2015, 1 page.

Notice of Allowance received for Canadian Patent Application No. 2,779,600, dated Jul. 7, 2017, 1 page.

Notice of Allowance received for Japanese Patent Application No. 2015-036444, dated Jan. 13, 2017, 3 pages (Official Copy Only).

Notice of Allowance received for Japanese Patent Application No. 2016-143049, dated Nov. 13, 2017, 3 pages (Official copy only).

Notice of Allowance received for Japanese Patent Application No. 2017-212658, dated May 13, 2019, 3 pages (Official Copy Only).

Notice of Allowance received for U.S. Appl. No. 14/515,130, dated May 2, 2016, 8 pages.

(56) References Cited

OTHER PUBLICATIONS

Notice of Allowance received for U.S. Appl. No. 14/515,130, dated May 25, 2016, 3 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 12/611,997, dated Apr. 15, 2015, 7 pages.
Notice of Allowance received for U.S. Appl. No. 13/207,381, dated Apr. 14, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 14/660,539, dated Apr. 6, 2018, 7 pages.
Notice of Allowance received for U.S. Appl. No. 14/693,155, dated Apr. 26, 2016, 9 pages.
Notice of Allowance received for U.S. Appl. No. 15/213,105, dated Aug. 10, 2018, 8 pages.
Notice of Allowance received for U.S. Appl. No. 13/615,107, dated Dec. 31, 2015, 10 pages.
Office Action received for Japanese Patent Application No. 2016-143049, dated Jul. 28, 2017, 7 pages (4 pages of English Translation and 3 pages of Official copy).
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2009313507, dated Nov. 13, 2013, 3 pages.
Office Action received for Canadian Patent Application No. 2,727,429, dated Apr. 14, 2015, 4 pages.
Office Action received for Canadian Patent Application No. 2,779,600, dated Jan. 4, 2016, 6 pages.
Office Action received for Canadian Patent Application No. 2,779,600, dated Oct. 19, 2016, 3 pages.
Office Action received for Chinese Patent Application No. 200980153687.X, dated Dec. 26, 2012, 11 pages of Official copy only.
Office Action received for Chinese Patent Application No. 200980153687.X, dated Jul. 11, 2013, 11 pages (Official copy only).
Office Action received for Chinese Patent Application No. 201380033808.3, dated Jul. 5, 2016. 9 pages (3 pages of English translation and 6 pages of Official copy).
Office Action received for Chinese Patent Application No. 201380041656.1, dated Jul. 5, 2016. 9 pages (4 pages of English translation and 5 pages of Official copy).
Office Action received for Chinese Patent Application No. 201380042887.4, dated Aug. 8, 2016, 9 pages (4 pages of English translation and 5 pages of Official copy).
Office Action received for European Patent Application No. 09763640.1, dated Dec. 2, 2016, 4 pages.
Office Action received for Japanese Patent Application No. 2011-513694, dated Aug. 27, 2013, 6 pages (3 pages of English Translation and 3 pages of Official copy).
Office Action Received for Japanese Patent Application No. 2011-513694, dated Jun. 10, 2014, 4 pages total (2 pages of Official Copy and 2 pages of English Translation) .
Office Action Received for Japanese Patent Application No. 2011-534914, dated Jan. 13, 2015, 9 pages(7 pages of English Translation and 2 pages of Official Copy.
Office Action Received for Japanese Patent Application No. 2011-534914, dated Jul. 15, 2014, 3 pages (1 page of English Translation and 2 pages of Official Copy).
Office Action received for Japanese Patent Application No. 2011-534914, dated May 10, 2016, 10 pages ( 4 pages of Official Copy and 6 pages of English Translation).
Office Action received for Japanese Patent Application No. 2011-534914, dated Oct. 1, 2013, 5 pages (2 pages of English Translation and 3 pages of Official copy).
Office Action received for Japanese Patent Application No. 2014-158517, dated Feb. 15, 2017, 8 pages (5 pages of English Translation and 3 pages of Official Copy Only).
Office Action Received for Japanese Patent Application No. 2014-158517, dated Jun. 22, 2017. 14 pages of official Copy only.
Office Action Received for Japanese Patent Application No. 2014-158517, dated May 19, 2015, 5 pages (2 pages of English Translation and 3 pages of Official Copy).
Office Action received for Japanese Patent Application No. 2015-036444, dated Feb. 23, 2016, 3 pages of English translation only.
Office Action received for Japanese Patent Application No. 2016-143049, dated Apr. 24, 2017. 5 pages ( 2 pages of English Translation and 3 pages of Official copy).
Office Action received for Japanese Patent Application No. 2017-212658, dated Dec. 20, 2018, 10 pages (6 pages of English Translation and 4 pages of Official Copy).
Office Action received for Japanese Patent Application No. 2017-212658, dated Sep. 12, 2018, 8 pages (5 pages of English Translation and 3 pages of Official Copy).
Office Action received for Japanese Patent Application No. 2017-212659, dated Jul. 5, 2018, 2 pages (Official Copy Only).
Office Action received for Japanese Patent Application No. 2017-212659, dated Mar. 4, 2019, 2 pages (Official Copy Only).
Office Action received for Japanese Patent Application No. 2015-036444, dated Sep. 14, 2016, 5 pages (3 Pages of English Translation and 2 Pages of Official Copy).
Office Action received for Japanese Patent Application No. 2016-094326, dated Dec. 2, 2016, 4 pages (2 pages of English Translation and 2 pages Official Copy Only).
Office Action received for Japanese Patent Application No. 2016-094326, dated Jul. 6, 2017, 2 pages (Official Copy Only).
Operator's Manual Intravascular Lithotripsy (IVL) Generator and Connector Cable LBL 61876 Rev. E Mar. 2018, pp. 1-16.
Optical Coherence Tomography Assessment of the Mechanistic Effects of Rotational and Orbital Atherectomy in Severely Calcified Coronary Lesions, Catheterization and Cardiovascular Interventions, vol. 86, 2015, pp. 1024-1032.
Oral Argument *Cardiovascular Systems Inc.* vs. *Shockwave Medical Inc.* in Inter Partes Review No. IPR2019-00405, dated May 8, 2019, 35 pages.
Otsuka et al., "Has Our Understanding of Calcification in Human Coronary Atherosclerosis Progressed", Coronary Calcification, Apr. 2014, pp. 724-738.
Patent Owner Preliminary Response for U.S. Pat. No. 8,956,371, by the Patent Trial and Appeal Board dated Apr. 10, 2019, 79 pages.
Patent Owner Sur-Reply for U.S. Pat. No. 8,956,371, by the Patent Trial and Appeal Board dated May 24, 2019, 8 pages.

(56) References Cited

OTHER PUBLICATIONS

Patent Owner's Response dated Nov. 7, 2019, 70 pages.
Patent Owner's Response Case No. IPR2019-00409 dated Nov. 3, 2019, 65 pages.
Patent Owner's Updated Exhibit List for U.S. Pat. No. 8,956,371, by the Patent Trial and Appeal Board dated May 24, 2019, 7 pages.
Patent Owner's Sur-Reply for U.S. Pat. No. 8,956,371, by the Patent Trial and Appeal Board dated Mar. 20, 2020, Mar. 20, 2020, 53 pages.
Patent Owner's Updated Exhibit List for U.S. Pat. No. 8,956,371, by the Patent Trial and Appeal Board dated Mar. 20, 2020, 18 pages.
Patterson et al., (1985). "The Etiology and Treatment of delayed Bleeding following Percutaneous Lithotripsy," The Journal of Urology, 133:447-451.
Peripheral Diamondback 360 Peripheral OAS, Micro Crown, Patents, Cardiovascular Systems, Inc., 201 T, 6 pages.
Peripheral Intravascular Lithotripsy (IVL) Catheter—Instructions for Use (IFU) LBL 61932, Rev A Instructions for Use US Jan. 2018, pp. 1-5.
Peripheral Intravascular Lithotripsy (IVL) Catheter Instructions for Use (IFU) LBL 61959, Rev. B Instructions for Use Jun. 2018, pp. 1-7.
Peripheral IVL Case Setup and Execution Shockwave Medical Inc., Available Online at <http://shockwavemedical.com/wp-content/uploads/2018/12/PAD-IVL-Case-Set-Up.pdf>, pp. 1-11.
Petition for Inter Partes Review for U.S. Pat. No. 8,956,371, issued on Feb. 17, 2015, 75 pages.
Petitioner Power of Attorney for U.S. Pat. No. 8,956,371, dated Dec. 6, 2018, pp. 1-2.
Petitioner's Reply Brief Case IPR2019-00405 Feb. 21, 2020, 65 pages.
Petitioner's Reply to Patent Owner's Preliminary Response for U.S. Pat. No. 8,956,371, by the Patent Trial and Appeal Board dated May 15, 2019, 7 pages.
Press Release: Shockwave Medical Reports Fourth Quarter and Full Year 2019 Financial Results and Provides Full Year 2020 Financial Outlook, Mar. 4, 2020, 7 pages.
Press Release: St. Francis Participates in Landmark Study Using Sonic Pressure Waves to Treat Heart Blockages, Catholic Health, Jan. 17, 2019, 5 pages.
Publicly available Professional & Educational Background Summary for Clifton Alferness Exhibit 1229 2013, 3 pages.
Publicly available Professional & Educational Background Summary for Daniel Hawkins Exhibit 1226, 2018, 2 pages.
Publicly available Professional & Educational Background Summary for Guy Levy Exhibit 1253 2019, 2 pages.
Publicly available Professional & Educational Background Summary for John Adams Exhibit 1221, 2009, 2 pages.
Publicly available Professional & Educational Background Summary for Krishna Bhatta Exhibit 1251 2005, 2 pages.
Publicly available Professional & Educational Background Summary for Marat Izrailevich Lerner 2020, 3 pages.
Publicly available Professional & Educational Background Summary for Marat Lerner 2008-2020, 4 pages.
Publicly available Professional & Educational Background Summary for Naoki Uchiyama 2020, 2 pages.
Publicly available Professional & Educational Background Summary for Ralph de la Torre Exhibit 1252 2010, 2 pages.
Publicly available Professional & Educational Background Summary for Robert Mantell Exhibit 1256 2000, 2 pages.
Publicly available Professional & Educational Background Summary for Stepan Khachin 2008-2020, 3 pages.
Publicly available Professional & Educational Background Summary for Valery Diamant Exhibit 1257 2017, 2 pages.
Redline of Shockwave Provisional to Utility, pp. 1-6.
Response to Final Office Action received for U.S. Appl. No. 12/482,995, filed Sep. 19, 2011 Sep. 19, 2011, 20 pages.
Ricks, Delthia Long Island Doctors Using Sound Waves to Loosen Calcium Deposits from Arteries, Restore Blood Flow News/Health, Available Online at <https://www.newsday.com/news/health/calcium-treatment-st-francis-hospital-1.27314331> Feb. 15, 2019, p. 1-4.
Rocha-Singh, et al. Peripheral Arterial Calcification: Prevalence, Mechanism, Detection, and Clinical Implications Catheterization and Cardiovascular Interventions, vol. 86 2014 pp. E212-E220.
Rosenschein et al., (1992). "Shock-Wave Thrombus Ablation, a New Method for Noninvasive Mechanical Thrombolysis," The American Journal of Cardiology, 70:1358-1361.
Salunke et al., (2001). "Compressive Stress-Relaxation of Human Atherosclerotic Plaque," J Biomed Mater, 55:236-241.
Sasaki et al., (2015). New Insight into Scar-related Ventricular Tachycardia Circuits in Ischemic Cardiomyopathy: Fat Deposition after Myocardial Infarction on Computed Tomography, Heart Rhythm, 12(7):1508-1518.
Schenkman, Noah Ureter Anatomy WebMD LLC, Emedicine. medscape.com, Jul. 10, 2013, 8 pages.
Second Declaration of Natalie J. Grace dated May 24, 2019, pp. 1-2.
Shlofmitz et al., "Orbital Atherectomy a Comprehensive Review", Cardiol Clin vol. 8, 2019, pp. 161-171.
Shlofmitz et al., (2019). "Orbital Atherectomy: A Comprehensive Review," Interv Cardiol Clin, 8(2):161-171.
ShockwaveMedical.com Intravascular Lithotripsy (IVL) Available Online at <https://shockwavemedical.com/technology/intravascular-lithotripsy-ivl/?country=Egypt> 2019, pp. 1-4.
Simpson et al., (1962). "A New Catheter System for Coronary Angioplasty," The American Journal of Cardiology, 49:1216-1222.
Smith et al., (1992). "Microwave Thermal Balloon Angioplasty in the Normal Rabbit," American Heart Journal, 123(6):1516-1521.
Sokol (2011). "Clinical Anatomy of the Uterus, Fallopian Tubes, and Ovaries," Glob. Libr. Women's Med., pp. 1-12.
Soukas, "Deposition Transcript (compressed) of Peter Soukas, Cases:—IPR2019-00405, IPR2019-00408, IPR2019-00409," Dec. 30, 2019, 10 pages.
Stephens, William, "Deposition Transcript (compressed) of William Patrick Stephens Case No. IPR2019-00408," Jan. 22, 2020, 55 pages.
Supplemental Declaration of Dr. Morten Olgaard Jensen Case IPR2019-00405 Feb. 21, 2020, 136 pages.
Tanaka et al., (2001). "A New Radiofrequency Thermal Balloon Catheter for Pulmonary Vein Isolation," Journal of the American College of Cardiology, 38(7):2079-2086.
Thiem et al., (2018). "The 12-Month Results of the EffPac Trial," Journal of Vascular Surgery, 68(55):e122-e123.
Top Cardiovascular Innovation Award Cardiovascular Research Technologies (CRT) 2015, 1 page.
WebMD.com Definition of 'Angioplasty' Available Online at <https://www.webmd.com/heart-disease/heart-failure/qa/what-is-the-definition-of-angioplasty> Oct. 29, 2017, pp. 1-2.
Weide, Daniel Deposition Transcript (compressed) of Daniel van der Weide, Ph.D. Exhibit 1203, Case No. IPR2019-00408, U.S. Pat. No. 9,642,673 B2 Jan. 13, 2020, 94 pages.
Wells Fargo Securities LLC SWAV: Initiating With a Market Perform Rating Shockwave Medical Inc. Apr. 1, 2019, pp. 1-34.
Yamamoto et al., (2018). "Effect of orbital atherectomy in calcified coronary artery lesions as assessed by optical coherence tomography," Catheter Cardiovasc Interv, 93(7):1211-1218.
Zhong et al., (1997). "Publication Information—Transient Oscillation of Cavitation Bubbles Near Stone Surface During Electrohydraulic Lithotripsy," Journal of Endourology, 11, 1 page.
Zhong et al., (1997). "Transient Oscillation of Cavitation Bubbles Near Stone Surface During Electrohydraulic Lithotripsy," Journal of Endourology, 11(1):55-61.
Corrected Notice of Allowance received for U.S. Appl. No. 16/544,516, dated May 26, 2020, 5 pages.
Final Office Action received for U.S. Appl. No. 16/183,438, dated Aug. 11, 2020, 12 pages.
Hawkins, et al. U.S. Appl. No. 61/061,170, pp. 1-50.
International Preliminary Report on Patentability received for PCT Patent Application No. PCT/US2013/054104 dated Feb. 19, 2015, 8 pages.
International Search Report and Written Opinion received for PCT Patent Application No. PCT/US2015/060453, dated Jan. 21, 2016, 15 pages.

(56) References Cited

OTHER PUBLICATIONS

Mantell U.S. Appl. No. 61/051,262 20 pages.
Non-Final Office Action received for U.S. Appl. No. 13/962,315, dated Aug. 26, 2015, 20 pages.
Non-Final Office Action received for U.S. Appl. No. 16/183,438, dated Mar. 31, 2020, 11 pages.
Notice of Allowance received for U.S. Appl. No. 16/028,225, dated Dec. 10, 2020, 8 pages.
Notice of Allowance received for U.S. Appl. No. 16/183,438, dated Jan. 14, 2021, 8 pages.
Notice of Allowance received for U.S. Appl. No. 16/544,516, dated May 5, 2020, 7 pages.
Third Party Preissuance Submission for U.S. Appl. No. 16/028,225, filed Aug. 2, 2019, 7 pages.
Third-Party Submission Under 37 CFR 1.290 Concise Description of Relevance for U.S. Appl. No. 16/028,225, filed Aug. 2, 2019, 4 pages.
U.S. Unpublished U.S. Appl. No. 17/231,936, filed Apr. 15, 2021, titled "Shockwave Valvuloplasty Catheter System," (Copy not submitted herewith pursuant to the waiver of 37 C.F.R. § 1.98(a)(2)(iii)).
Notice Concerning Request for Invalidation against Chinese Patent No. ZL2000980153687.X dated Mar. 29, 2022, 61 pages. English translation.
Final Written Decision, IPR2019-00405, U.S. Pat. No. 8,956,371.†

\* cited by examiner
† cited by third party

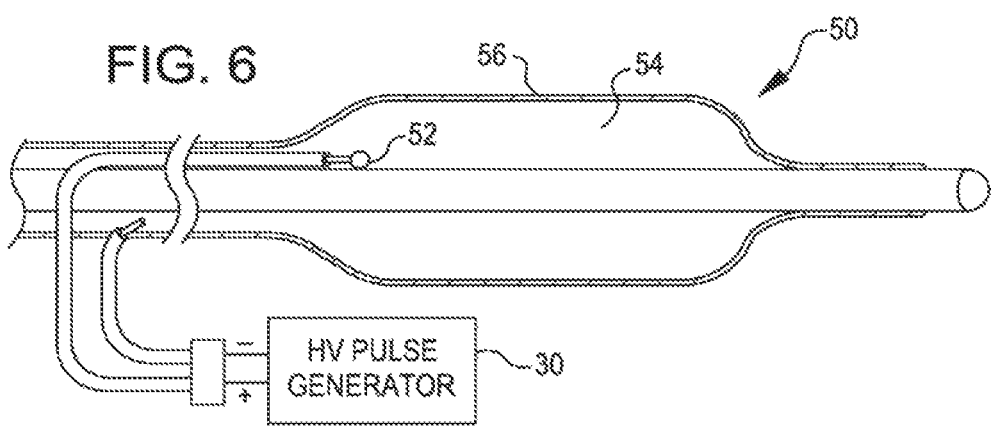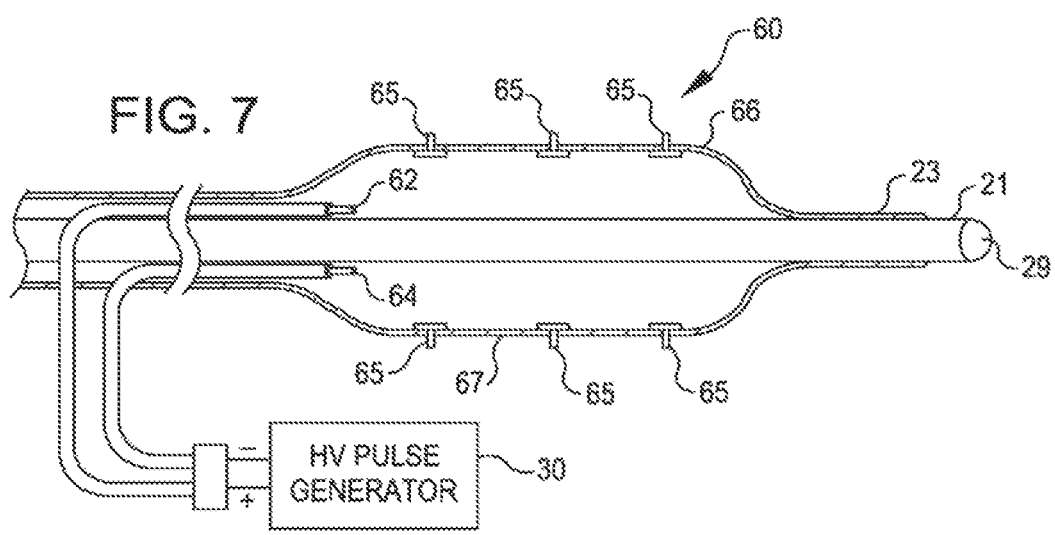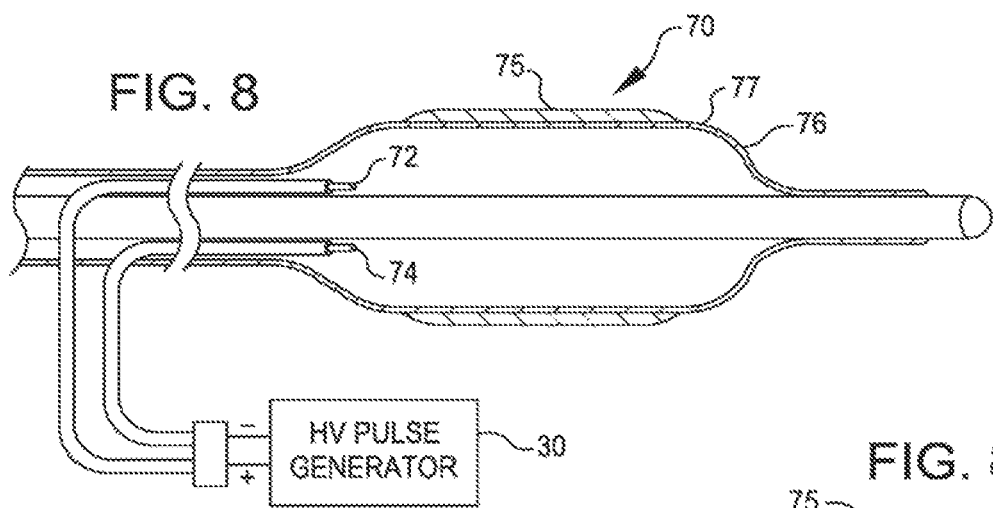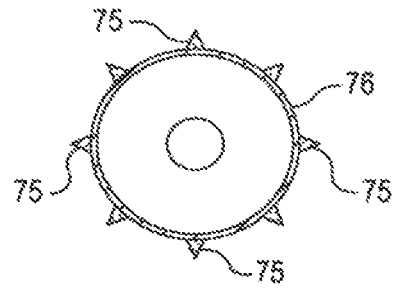

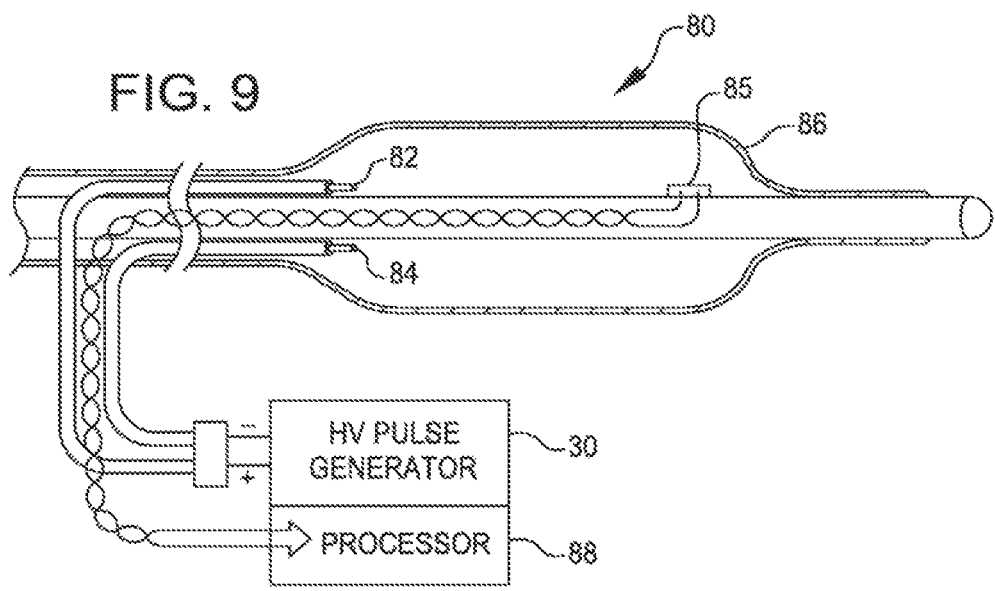
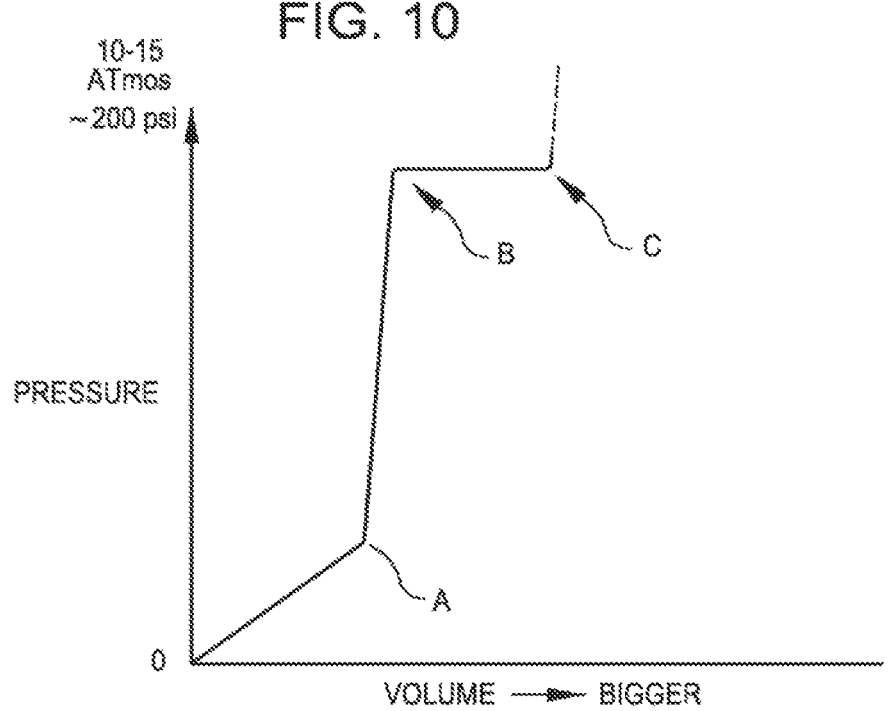

SHOCKWAVE BALLOON CATHETER SYSTEM

PRIORITY CLAIM

The present application is a continuation of U.S. patent application Ser. No. 16/028,225, filed Jul. 5, 2018, which is a continuation of U.S. patent application Ser. No. 14/660,539, filed Mar. 17, 2015, now issued as U.S. Pat. No. 10,039,561, on Aug. 7, 2018, which is a continuation of U.S. patent application Ser. No. 13/646,570, filed Oct. 5, 2012, now issued as U.S. Pat. No. 9,011,462, on Apr. 21, 2015, which is a continuation of U.S. patent application Ser. No. 12/482,995, filed Jun. 11, 2009, now issued as U.S. Pat. No. 8,956,371 on Feb. 17, 2015, which claims the benefit of U.S. Provisional Patent Application Ser. No. 61/061,170, filed Jun. 13, 2008, each of which is incorporated herein by reference in its entirety.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the open in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

SUMMARY OF THE INVENTION

The invention provides a catheter that comprises an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon.

The at least one electrode may include a single metallic electrode of a pair of metallic electrodes. The electrodes may be radially displaced from each other or longitudinally displaced from each other. The at least one electrode may be formed of stainless steel.

The balloon may be formed of non-compliant material or of compliant material. The dilating balloon may have at least one stress riser carried on its surface.

The catheter may further comprise a sensor that senses reflected energy. The sensor may be distal to the at least one electrode. The sensor may be disposed on the carrier.

The catheter may further comprise a reflector within the dilating balloon that focuses the shock waves. The reflector may form one of the at least one electrodes. The catheter has a center line and the reflector may be arranged to focus the shock waves off of the catheter center line.

The fluid may be saline. The fluid may include an x-ray contrast.

The catheter may further include a lumen for receiving a guide wire. The lumen may be defined by the carrier.

The invention further provides a system comprising a catheter including an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon. The system further comprises a power source that provides electrical energy to the arc generator.

The power source is preferably arranged to provide pulsed high voltage. The power source may be arranged to provide high voltage pulses having selectable pulse durations, selectable voltage amplitudes, and/or selectable pulse repetition rates.

The system may further comprise an R wave detector that synchronizes the mechanical shock waves with cardiac P waves.

The at least one electrode may include a single metallic electrode of a pair of metallic electrodes. The electrodes may be radially displaced from each other or longitudinally displaced from each other. The at least one electrode may be formed of stainless steel.

The balloon may be formed of non-compliant material or of compliant material. The dilating balloon may have at least one stress riser carried on its surface.

The catheter may further comprise a sensor that senses reflected energy. The sensor may be distal to the at least one electrode. The sensor may be disposed on the carrier.

The catheter may further comprise a reflector within the dilating balloon that focuses the shock waves. The reflector may form one of the at least one electrodes. The catheter has a center line and the reflector may be arranged to focus the shock waves off of the catheter center line.

The fluid may be saline. The fluid may include an x-ray contrast.

The catheter may further include a lumen for receiving a guide wire. The lumen may be defined by the carrier.

The invention further provides a method comprising the step of providing a catheter including an elongated carrier, a dilating balloon about the carrier in sealed relation thereto, the balloon being arranged to receive a fluid therein that inflates the balloon, and an arc generator including at least one electrode within the balloon that forms a mechanical shock wave within the balloon. The method further comprises the steps of inserting the catheter into a body lumen of a patient adjacent an obstruction of the body lumen, admitting fluid into the balloon, and applying high voltage pulses to the arc generator to form a series of mechanical shocks within the balloon.

The method may include the further step of detecting cardiac R waves of the patient's heart, and synchronizing the mechanical shocks with the detected P waves.

The method may further include the step of varying one of the repetition rate, amplitude and duration of the high voltage pulses to vary the intensity of the mechanical shock waves.

The method may include the further step of sensing reflected energy within the catheter.

The method may include the further step of placing a guide wire into the body lumen and guiding the catheter into the body lumen along the guide wire.

The method may include the further step of focusing the mechanical shockwaves. The mechanical shockwaves may be focused away from the catheter center axis.

The method may include the further steps of adding an x-ray contrast to the fluid and visualizing the catheter under fluoroscopy.

BRIEF DESCRIPTION OF THE DRAWINGS

For illustration and not limitation, some of the features of the present invention are set forth in the appended claims. The various embodiments of the invention, together with representative features and advantages thereof, may best be understood by making reference to the following description taken in conjunction with the accompanying drawings, in the several figures of which like reference numerals identify identical elements, and wherein:

FIG. 6 is a side view of a dilating catheter with insulated electrodes within the balloon displaced with a single pole in the balloon and a second being the ionic fluid inside the balloon according to a further embodiment of the invention.

FIG. 7 is a side view of a dilating catheter with insulated electrodes within the balloon and studs to reach the calcification according to a still further embodiment of the invention.

FIG. 8 is a side view of a dilating catheter with insulated electrodes within the balloon with raised ribs on the balloon according to still another embodiment of the invention.

FIG. 8A is a front view of the catheter of FIG. 8.

FIG. 9 is a side view of a dilating catheter with insulated electrodes within the balloon and a sensor to detect reflected signals according to a further embodiment of the invention.

FIG. 10 is a pressure volume curve of a prior art balloon breaking a calcified lesion.

DETAILED DESCRIPTION OF THE INVENTION

Figure 1:
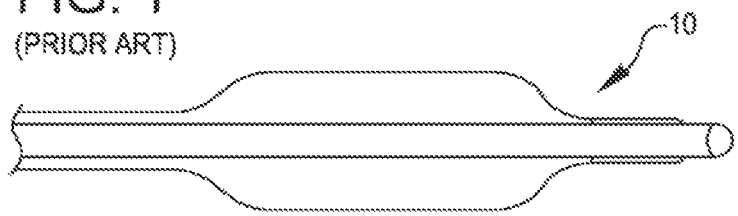
FIG. 1 is a view of the therapeutic end of a typical prior art over-the-wire angioplasty balloon catheter.

FIG. 1 is a view of the therapeutic end of a typical prior art over-the-wire angioplasty balloon catheter 10. Such catheters are usually non-complaint with a fixed maximum dimension when expanded with a fluid such as saline.

Figure 2:
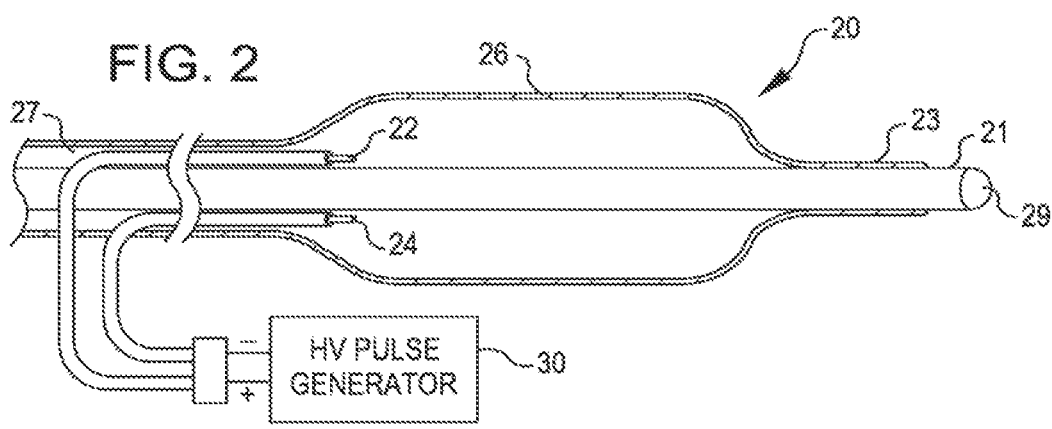
FIG. 2 is a side view of a dilating angioplasty balloon catheter with two electrodes within the balloon attached to a source of high voltage pulses according to one embodiment of the invention.

FIG. 2 is a view of a dilating angioplasty balloon catheter 20 according to an embodiment of the invention. The catheter 20 includes an elongated carrier, such as a hollow sheath 21, and a dilating balloon 26 formed about the sheath 21 in sealed relation thereto at a seal 23. The balloon 26 forms an annular channel 27 about the sheath 21 through which fluid, such as saline, may be admitted into the balloon to inflate the balloon. The channel 27 further permits the balloon 26 to be provided with two electrodes 22 and 24 within the fluid filled balloon 26. The electrodes 22 and 24 are attached to a source of high voltage pulses 30. The electrodes 22 and 24 are formed of metal, such as stainless steel, and are placed a controlled distance apart to allow a reproducible arc for a given voltage and current. The electrical arcs between electrodes 22 and 24 in the fluid are used to generate shock waves in the fluid. The variable high voltage pulse generator 30 is used to deliver a stream of pulses to the electrodes 22 and 24 to create a stream of shock waves within the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing of the catheter during use. The carrier 21 includes a lumen 29 through which a guidewire (not shown) may be inserted to guide the catheter into position. Once positioned the physician or operator can start with low energy shock waves and increase the energy as needed to crack the calcified plague. Such shockwaves will be conducted through the fluid, through the balloon, through the blood and vessel wall to the calcified lesion where the energy will break the hardened plaque without the application of excessive pressure by the balloon on the walls of the artery.

Figure 3:
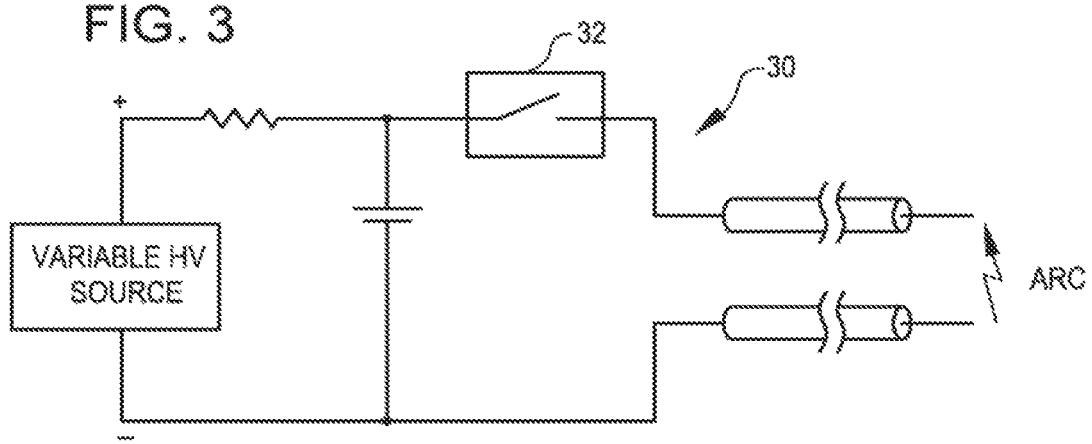
FIG. 3 is a schematic of a high voltage pulse generator.
Figure 3A:
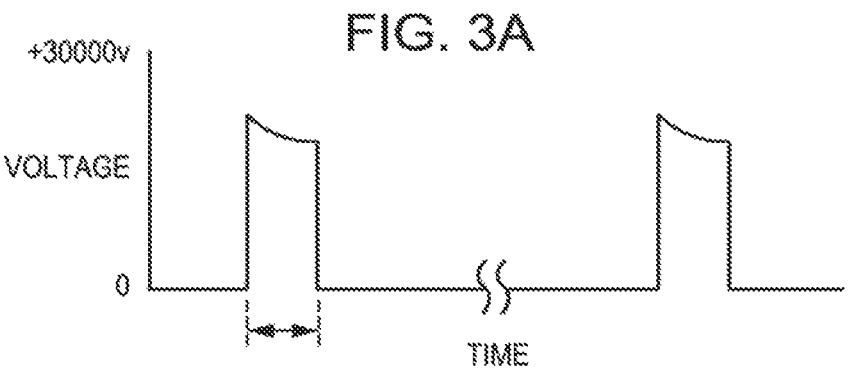
FIG. 3A shows voltage pulses that may be obtained with the generator of FIG. 3.

FIG. 3 is a schematic of the high voltage pulse generator 30. FIG. 3A shows a resulting waveform. The voltage needed will depend on the gap between the electrodes and generally 100 to 3000 volts. The high voltage switch 32 can be set to control the duration of the pulse. The pulse duration will depend on the surface area of the electrodes 22 and 24 and needs to be sufficient to generate a gas bubble at the surface of the electrode causing a plasma arc of electric current to jump the bubble and create a rapidly expanding and collapsing bubble, which creates the mechanical shock wave in the balloon. Such shock waves can be as short as a few microseconds.

Figure 4:
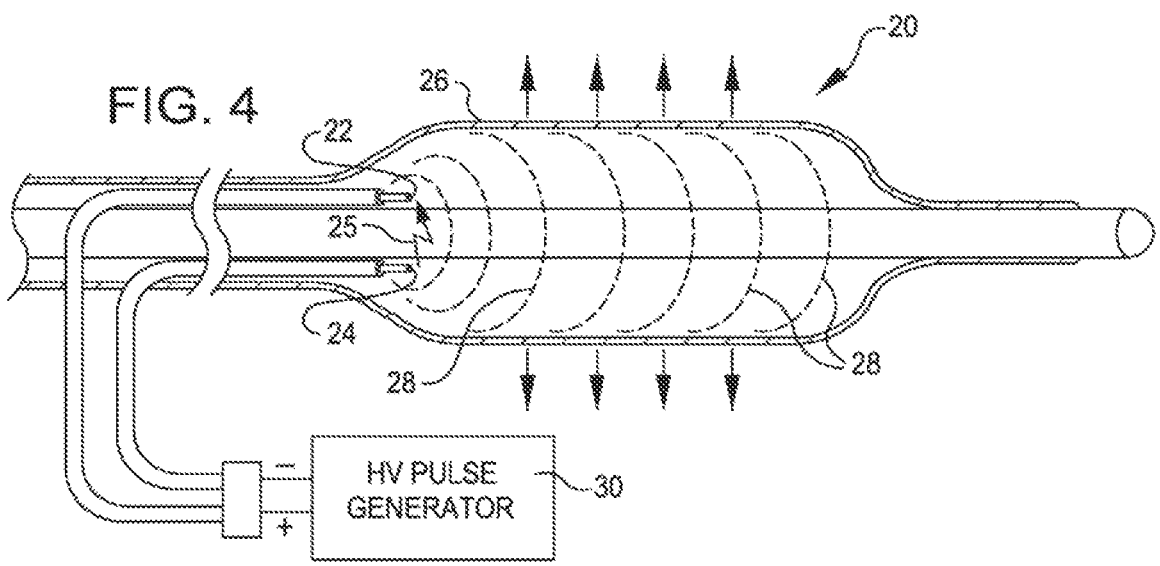
FIG. 4 is a side view of the catheter of FIG. 2 showing an arc between the electrodes and simulations of the hock wave flow.

FIG. 4 is a cross sectional view of the shockwave catheter 20 showing an arc 25 between the electrodes 22 and 24 and simulations of the shock wave flow 28. The shock wave 28 will radiate out from the electrodes 22 and 24 in all directions and will travel through the balloon 26 to the vessel where it will break the calcified lesion into smaller pieces.

Figure 5:
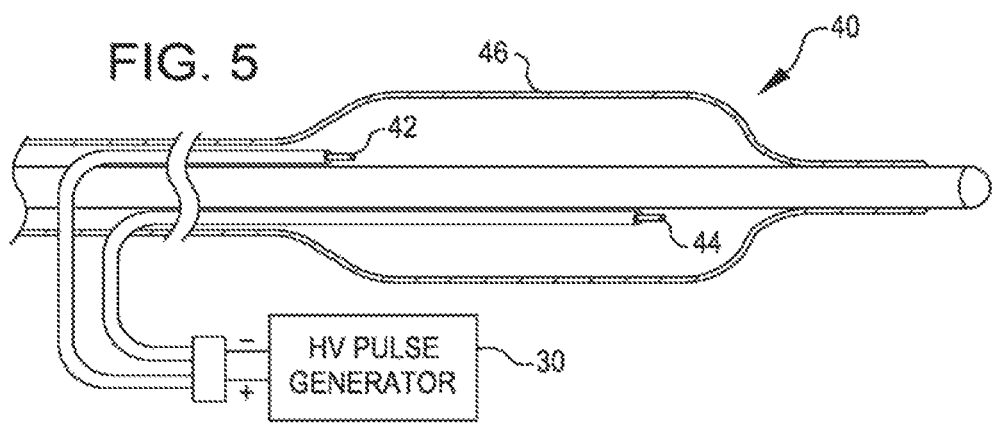
FIG. 5 is a side view of a dilating catheter with insulated electrodes within the balloon and displaced along the length of the balloon according to another embodiment of the invention.

FIG. 5 shows another dilating catheter 40. It has insulated electrodes 42 and 44 within the balloon 46 displaced along the length of the balloon 46.

FIG. 6 shows a dilating catheter 50 with an insulated electrode 52 within the balloon 56. The electrode is a single electrode pole in the balloon, a second pole being the ionic fluid 54 inside the balloon. This unipolar configuration uses the ionic fluid as the other electrical pole and permits a smaller balloon and catheter design for low profile balloons. The ionic fluid is connected electrically to the HV pulse generator 30.

FIG. 7 is another dilating 60 catheter with electrodes 62 and 64 within the balloon 66 and studs 65 to reach the calcification. The studs 65 form mechanical stress risers on the balloon surface 67 and are designed to mechanically conduct the shock wave through the intimal layer of tissue of the vessel and deliver it directly to the calcified lesion.

FIG. 8 is another dilating catheter 70 with electrodes 72 and 74 within the balloon 76 and with raised ribs 75 on the surface 77 of the balloon 76. The raised ribs 75 (best seen in FIG. 8A) form stress risers that will focus the shockwave energy to linear regions of the calcified plaque.

FIG. 9 is a further dilating catheter 80 with electrodes 82 and 84 within the balloon 86. The catheter 80 further includes a sensor 85 to detect reflected signals. Reflected signals from the calcified plaque can be processed by a processor 88 to determine quality of the calcification and quality of pulverization of the lesion.

Figure 10A:
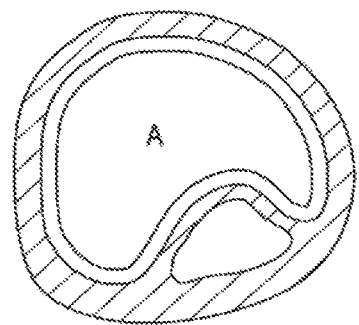
FIG. 10A is a sectional view of a balloon expanding freely within a vessel.
Figure 10B:
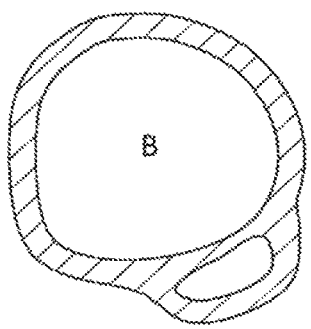
FIG. 10B is a sectional view of a balloon constrained to the point of breaking in a vessel.
Figure 10C:
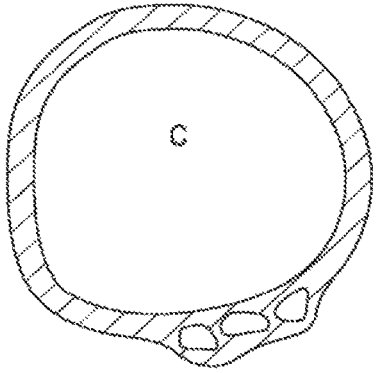
FIG. 10C is a sectional view of a balloon after breaking within the vessel.
Figure 11:
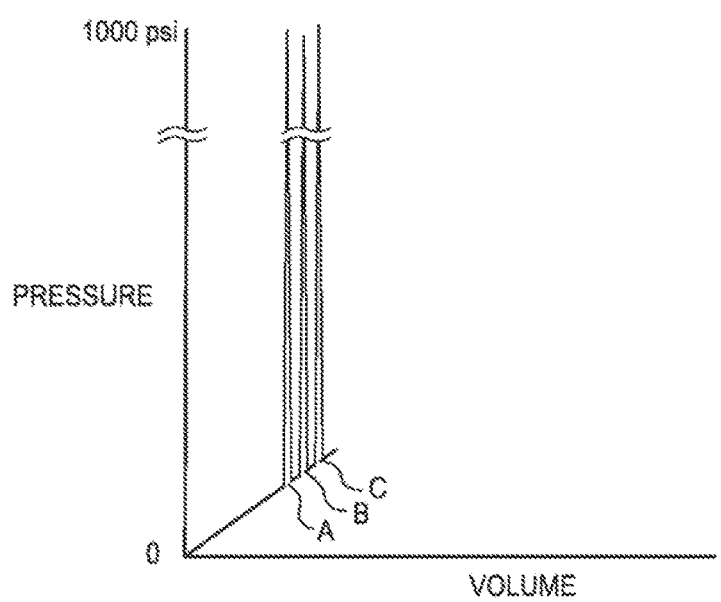
FIG. 11 is a pressure volume curve showing the various stages in the breaking of a calcified lesion with shock waves according to an embodiment of the invention.
Figure 11A:
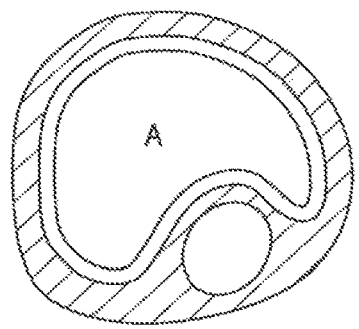
FIG. 11A is a sectional view showing a compliant balloon within a vessel.
Figure 11B:
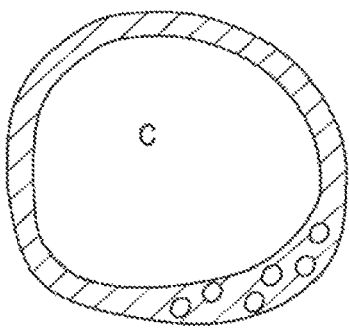
FIG. 11B is a sectional view showing pulverized calcification on a vessel wall.

FIG. 10 is a pressure volume curve of a prior art balloon breaking a calcified lesion. FIG. 10B shows the build up of energy within the balloon (region A to B) and FIG. 10C shows the release of the energy (region B to C) when the calcification breaks. At region C the artery is expanded to the maximum dimension of the balloon. Such a dimension can lead to injury to the vessel walls. FIG. 10A shows the initial inflation of the balloon, FIG. 11 is a pressure volume curve showing the various stages in the breaking of a calcified lesion with shock waves according to the embodiment. The balloon is expanded with a saline fluid and can be expanded to fit snugly to the vessel wall (Region A) (FIG. 11A) but this is not a requirement. As the High Voltage pulses generate shock waves (Region B and C) extremely high pressures, extremely short in duration will chip away the calcified lesion slowly and controllably expanding the opening in the vessel to allow blood to flow un-obstructed (FIG. 11B).

Figure 12:
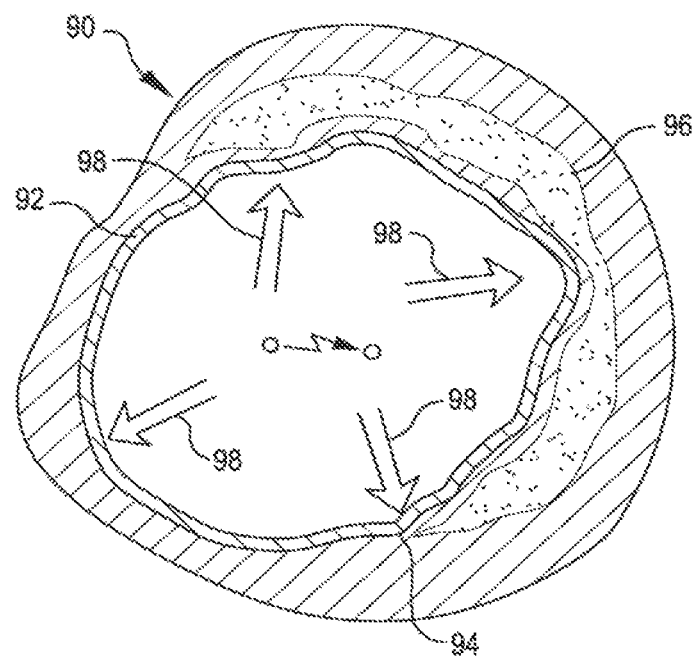
FIG. 12 illustrates shock waves delivered through the balloon wall and endothelium to a calcified lesion.

FIG. 12 shows, in a cutaway view, shock waves 98 delivered in all directions through the wall 92 of a saline filled balloon 90 and intima 94 to a calcified lesion 96. The shock waves 98 pulverize the lesion 96. The balloon wall 92 may be formed of non-compliant or compliant material to contact the intima 94.

Figure 13:
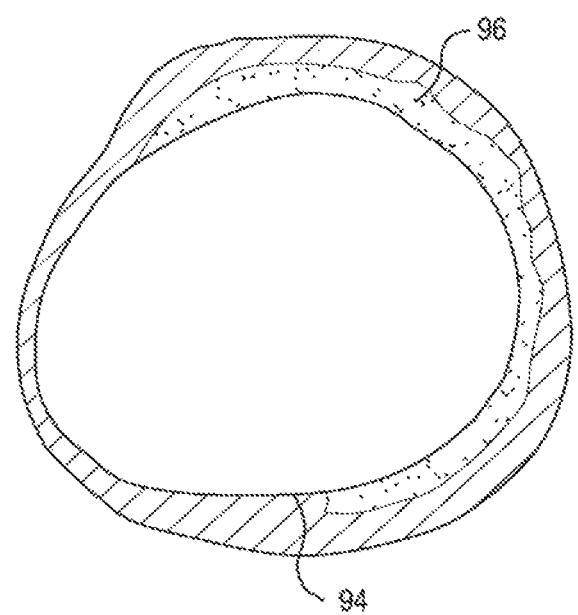
FIG. 13 shows calcified plaque pulverized and smooth a endothelium restored by the expanded balloon after pulverization.

FIG. 13 shows calcified plaque 96 pulverized by the shock waves. The intima 94 is smoothed and restored after the expanded balloon (not shown) has pulverized and reshaped the plaque into the vessel wall.

Figure 14:
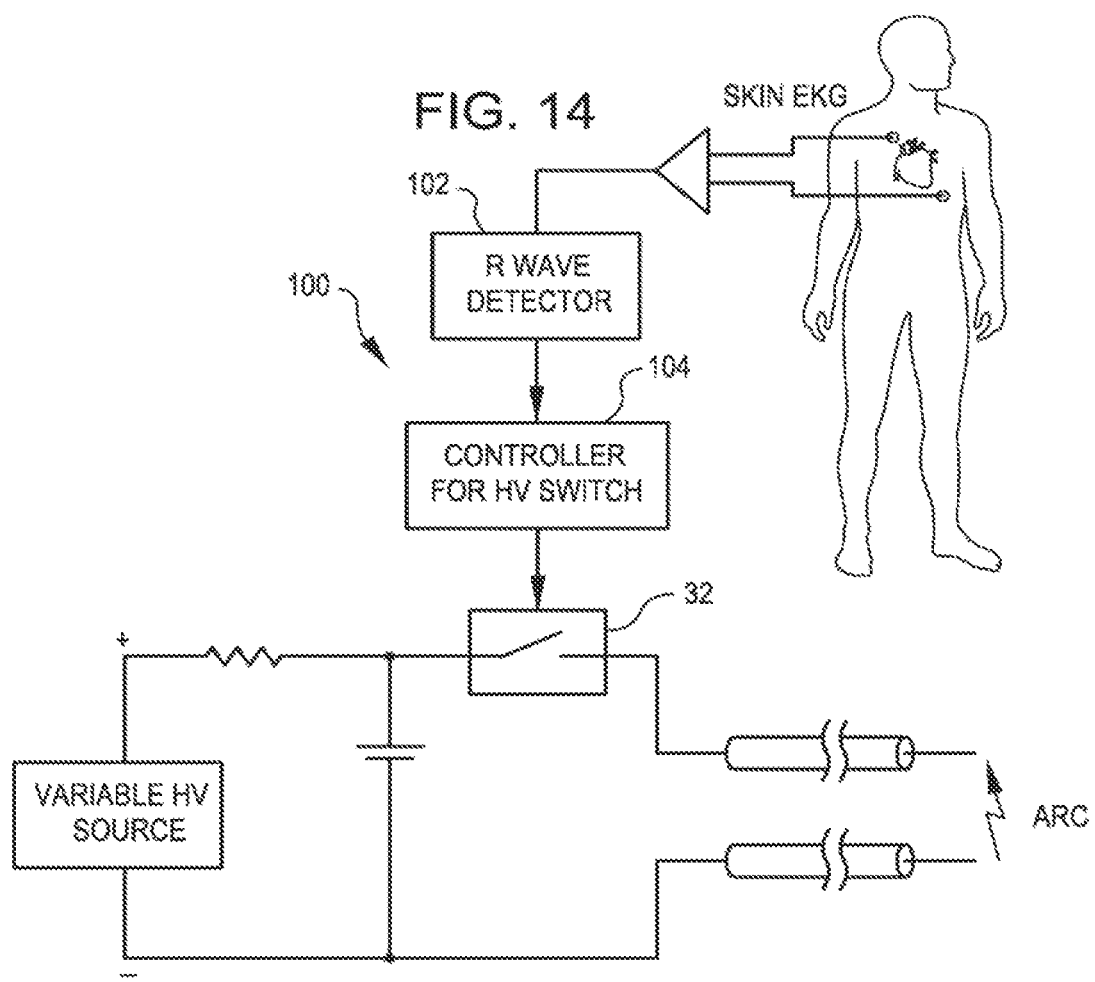
FIG. 14 is a schematic of a circuit that uses a surface EKG to synchronize the shock wave to the "R" wave for treating vessels near the heart.

FIG. 14 is a schematic of a circuit 100 that uses the generator circuit 30 of FIG. 3 and a surface EKG 102 to synchronize the shock wave to the "R" wave for treating vessels near the heart. The circuit 100 includes an R-wave detector 102 and a controller 104 to control the high voltage switch 32. Mechanical shocks can stimulate heart muscle and could lead to an arrhythmia. While it is unlikely that shockwaves of such short duration as contemplated herein would stimulate the heart, by synchronizing the pulses (or bursts of pulses) with the R-wave, an additional degree of safety is provided when used on vessels of the heart or near the heart. While the balloon in the current drawings will provide an electrical isolation of the patient from the current, a device could be made in a non-balloon or non-isolated manner using blood as the fluid. In such a device, synchronization to the R-wave would significantly improve the safety against unwanted arrhythmias.

Figure 15:
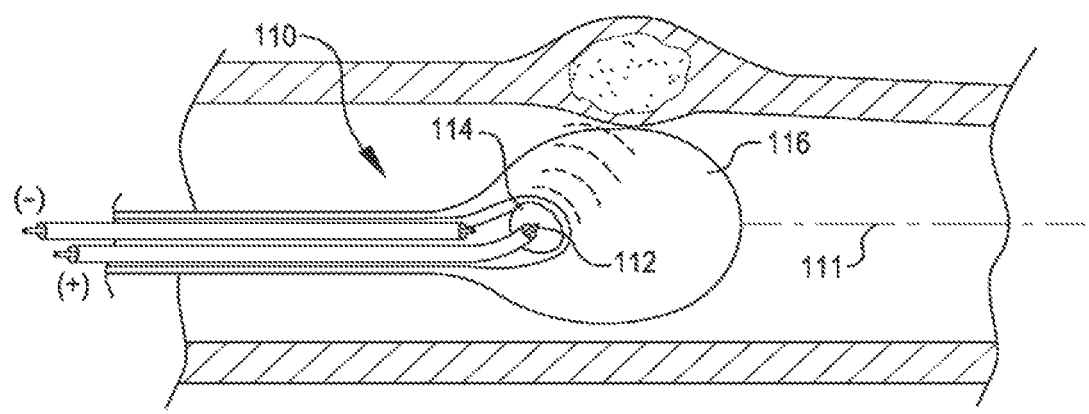
FIG. 15 is a side view, partly cut away, of a dilating catheter with a parabolic reflector acting as one electrode and provides a focused shock wave inside a fluid filled compliant balloon.

FIG. 15 shows a still further dilation catheter 110 wherein a shock wave is focused with a parabolic reflector 114 acting as one electrode inside a fluid filled compliant balloon 116. The other electrode 112 is located at the coaxial center of the reflector 114. By using the reflector as one electrode, the shock wave can be focused and therefore pointed at an angle (45 degrees, for example) off the center line 111 of the catheter artery. In this configuration, the other electrode 112 will be designed to be at the coaxial center of the reflector and designed to arc to the reflector 114 through the fluid. The catheter can be rotated if needed to break hard plaque as it rotates and delivers shockwaves.

While particular embodiments of the present invention have been shown and described, modifications may be made. For example, instead of manual actuation and spring loaded return of the valves used herein, constructions are possible which perform in a reversed manner by being spring actuated and manually returned. It is therefore intended in the appended claims to cover all such changes and modifications which fall within the true spirit and scope of the invention as defined by those claims.

What is claimed is:

1. A method of treating calcified lesions in the wall of a vessel comprising the steps of:
providing a catheter including a hollow sheath for receiving a guidewire, said catheter including a dilating balloon sealed at the distal end thereof, said dilating balloon being fillable with a liquid, said catheter further including a pair of spaced apart electrodes located within the balloon and outside the hollow sheath;
advancing the catheter into the vessel until the balloon is in proximity to the calcified lesion;
inflating the balloon with the liquid to fix the balloon to the wall of the vessel;
supplying a voltage pulse across the electrode pair, the pulse have a duration on the order of microseconds, the voltage pulse having sufficient energy to create a plasma arc across the spaced apart electrodes resulting in the formation of a shock wave that passes through the balloon to the calcified lesion; and
repeating the supplying step a plurality of times sufficient to crack the calcified lesion with the shock waves such that the dilating balloon expands the vessel.

2. The method of claim 1 wherein said advancing step is performed by advancing the catheter over a guide wire positioned within the hollow sheath.

3. The method of claim 1 where the voltage pulse is between 100 and 1,000 volts.

4. The method of claim 1 wherein the electrode pair is spaced apart radially.

5. The method of claim 1 wherein the electrode pair is spaced apart longitudinally.

6. The method of claim 1 wherein cracking of the calcified lesion comprises pulverizing at least a portion of the calcified lesion.

7. The method of claim 1 wherein the liquid is conductive.

8. The method of claim 1 wherein the liquid is saline.

9. The method of claim 1 wherein one electrode in the pair is larger than the other electrode in the pair.

10. The method of claim 1 further including a power source for supplying high voltage pulses to the electrodes.

11. The method of claim 1 further including sensing reflecting signals to determine the quality of the calcification and/or the quality of the pulverization of the calcified lesion.

12. The method of claim 1 wherein said catheter further includes a reflector for directing the angle of the shock waves.

* * * * *